(12) United States Patent
Johannesen et al.

(10) Patent No.: US 9,403,059 B1
(45) Date of Patent: Aug. 2, 2016

(54) SYSTEM AND METHOD FOR FITTING GOLF CLUBS

(71) Applicant: Pro-Fit Performance Club Fitting, L.L.C., Lincoln, NE (US)

(72) Inventors: Greg Johannesen, Lincoln, NE (US); James B. White, Lincoln, NE (US)

(73) Assignee: Pro-Pit Performance Club Fitting, L.L.C., Lincoln, NE (US)

( * ) Notice: Subject to any disclaimer, the term of this patent is extended or adjusted under 35 U.S.C. 154(b) by 0 days.

(21) Appl. No.: 14/948,751

(22) Filed: Nov. 23, 2015

Related U.S. Application Data (63) Continuation-in-part of application No. 14/445,753, filed on Jul. 29, 2014, now Pat. No. 9,192,836.

(60) Provisional application No. 61/861,058, filed on Aug. 1, 2013.

(51) Int. Cl.
 A63B 60/42 (2015.01)
 A63B 24/00 (2006.01)

(52) U.S. Cl.
 CPC .................... *A63B 24/0003* (2013.01)

(58) Field of Classification Search
 CPC .. A63B 53/00; A63B 53/06; A63B 2053/005; A63B 2059/0018; A63B 2059/004
 USPC ............................ 463/42; 473/291, 292, 409
 See application file for complete search history.

(56) References Cited

U.S. PATENT DOCUMENTS

| | | |
|---|---|---|
| 7,153,215 B2 | 12/2006 | Peterson et al. |
| 7,195,565 B2 | 3/2007 | White et al. |
| 8,827,842 B2 | 9/2014 | Voges et al. |

*Primary Examiner* — Allen Chan
(74) *Attorney, Agent, or Firm* — Tyson B. Benson; Advent, LLP (57) ABSTRACT

A system and method for fitting golf clubs is disclosed. The system and method implement a unique swing weight scale for promoting improved fitting, and thus, improved performance of the golf clubs.

12 Claims, 5 Drawing Sheets

6 iron Length: 37.75

Initial Set specifications — A-1

| club | Length | Dwt(g) | Dwt(oz) | 7.75"gm | Bl.2-7.75" (initial) |
|---|---|---|---|---|---|
| Dr | 45.00 | 320 | 11.29 | 1007 | .740 |
| 3w | 43.00 | 338 | 11.92 | 1016 | .741 |
| 17*hyb | 41.00 | 366 | 12.91 | 1026 | .737 |
| 19*hyb | 40.50 | 376 | 13.26 | 1049 | .750 |
| 21*hyb | 40.00 | 386 | 13.62 | 1050 | .746 |
| 3i | 39.25 | 418 | 14.74 | 1068 | .746 |
| 4i | 38.75 | 423 | 14.92 | 1070 | .744 |
| 5i | 38.25 | 428 | 15.10 | 1077 | .745 |
| 6i | 37.75 | 431 | 15.20 | 1080 | .745 |
| 7i | 37.25 | 439 | 15.49 | 1087 | .744 |
| 8i | 36.75 | 447 | 15.77 | 1092 | .743 |
| 9i | 36.25 | 456 | 16.08 | 1098 | .741 |
| Pw | 36.00 | 461 | 16.26 | 1104 | .742 |
| Gw | 35.63 | 465 | 16.40 | 1112 | .744 |
| Lw | 35.20 | 475 | 16.75 | 1123 | .745 |

Matching — A-2

| club | Bl.2-7.75" (ad'd) | Length | Dwt incr |
|---|---|---|---|
| Dr | .746 | 45.00 | 17 |
| 3w | .746 | 43.00 | 33 |
| 17*hyb | .746 | 41.00 | 14 |
| 19*hyb | .746 | 40.50 | 6 |
| 21*hyb | .746 | 40.00 | 32 |
| 3i | .746 | 39.25 | 6 |
| 4i | .746 | 38.75 | 4 |
| 5i | .746 | 38.25 | 4 |
| 6i | .746 | 37.75 | 7 |
| 7i | .746 | 37.25 | 7 |
| 8i | .746 | 36.75 | 11 |
| 9i | .746 | 36.25 | 4 |
| Pw | .746 | 36.00 | 5 |
| Gw | .746 | 35.63 | 9 |
| Lw | .746 | 35.20 | 0 |

FIG. 1A

| PXIII Matched Specifications | | | | PXIII | Swt | Swt | Current technology | | |
|---|---|---|---|---|---|---|---|---|---|
| Dwt(g) | Dwt(oz) | (Diff) Dwt(g) | (14" calibr) 7.75"gm | Lvpf diff | 14"gm | 14" | Lvpf sprd | Dwt sprd | Len sprd |
| 322 | 11.36 | 2 | 1013 | 6 | 448 | D4.4 | 8 | 17 | -2.00 |
| 339 | 11.96 | 1 | 1021 | 5 | 445 | D3.6 | 18 | 33 | -2.00 |
| 372 | 13.12 | 6 | 1039 | 13 | 444 | D3.3 | 5 | 8 | -0.50 |
| 380 | 13.40 | 4 | 1044 | -5 | 444 | D3.4 | 4 | 6 | -0.75 |
| 386 | 13.62 | 0 | 1048 | -2 | 443 | D3.1 | 19 | 32 | -0.50 |
| 418 | 14.74 | 0 | 1067 | -1 | 443 | D3.0 | 5 | 6 | -0.50 |
| 424 | 14.96 | 1 | 1072 | 2 | 444 | D3.3 | 4 | 4 | -0.50 |
| 428 | 15.10 | 0 | 1076 | -1 | 445 | D3.8 | 5 | 4 | -0.50 |
| 432 | 15.24 | 1 | 1081 | 1 | 448 | D4.4 | 6 | 7 | -0.50 |
| 439 | 15.49 | 0 | 1087 | 0 | 450 | D5.0 | 7 | 7 | -0.50 |
| 446 | 15.73 | -1 | 1094 | 2 | 451 | D5.3 | 10 | 11 | -0.50 |
| 457 | 16.12 | 1 | 1104 | 6 | 453 | D5.8 | 4 | 4 | -0.25 |
| 461 | 16.26 | 0 | 1108 | 4 | 455 | D6.4 | 5 | 5 | -0.37 |
| 466 | 16.44 | 1 | 1113 | 1 | 455 | D6.4 | 10 | 9 | -0.43 |
| 475 | 16.75 | 0 | 1123 | 0 | 456 | D6.7 | | | |

Dwt increment 3i-9i   ave
6.1

SYSTEM AND METHOD FOR FITTING GOLF CLUBS

BACKGROUND

The golf equipment industry continues to make quantum leaps in dub design and construction materials, with millions upon millions of dollars being poured into advertising of the new technology and further research and development to come up with even more technological advances, all to try to gain an edge in the highly competitive marketplace.

SUMMARY

A system and method for fitting golf clubs is disclosed. The system and method implement a unique swing weight scale for promoting improved fitting, and thus, improved performance of the golf clubs.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figure(s).

DETAILED DESCRIPTION

While companies have adopted a wide variety of design and performance concepts, one area which has become of primary importance is effective club fitting and the improvement of custom club building capabilities. However, the advances in club design have not been matched by similar advances in club fitting.

An improved golf club fitting system and method for fitting a set of golf clubs to a player includes the steps of measuring a player's hand grip strength and selecting a representative golf club having a dead weight directly proportional to the player's grip strength. The club length and the swing weight of the representative golf club are determined by standard testing procedures. However, in the fitting system of the present disclosure, rather than using the standard swing weight scale, which is based upon a 14 inch fulcrum and 21 inch club support (as measured from the grip end of the club), the fitting system/method of the present disclosure implements a unique swing weight scale, which is based upon a 7.75 inch fulcrum and 12 inch club support. The unique swing weight scale described herein more accurately reflects how a golf club is held and swung and how physical changes to the golf club affect the player and/or the player's performance. Using this unique swing weight scale allows for the golf club fitting system/process (e.g., PXIII method/process) described herein to be more accurate and efficient than previous golf club fitting systems/processes. Further, a Performance Index (e.g., Bi.2) for the representative golf club is then computed by using a polynomial equation featuring club length, club dead weight, and the Lpf (Leverage profile) value of the representative club to determine generally corresponding values for the remaining other golf clubs in the set such that the system user can match different irons and woods to the representative golf club thereby creating an ideal matched set of golf clubs for the player.

The present disclosure relates to systems and methods for custom fitting of golf clubs to players and, more particularly, to a golf club fitting system in which the club dead weight and balance are matched to each player's physical strength level, core-loading and swing type. The clubs within the player's set are weight and balanced matched for more consistent on-course performance.

The golf club fitting system and method described herein tests a player's grip strength and determines the proper dead weight of a golf club to be used based in part upon the grip strength. The selected golf club is measured to determine the swing weight (e.g., Lpf value) of the selected golf club, the swing weight scale being based upon a 7.75 inch fulcrum and 12 inch club support. The Performance Index (e.g., Bi.2) for the representative golf club is determined by using a polynomial equation featuring club length, club dead weight, and the Lpf (Leverage profile) value of the representative club. Significant player interviews and analyses are conducted during the fitting process for gathering information regarding preferred clubs, playing capabilities and player strengths and weaknesses in order to permit the user of the fitting system to make minor adjustments to the specific club set dictated by the numbers set forth by use of the present fitting system.

The present disclosure provides an improved golf club fitting system for fitting a set of golf clubs to a player including the steps of measuring a player's physical dimensions at least including grip strength of the player's hand and selecting a representative golf club having a specific dead weight based in part on the measured grip strength of the player's hand, the dead weight being directly proportional to the player's grip strength, specifically that the dead weight of the golf club is greater when the player's grip strength is greater and vice versa. The club length of the representative golf club is then recorded and the swing weight of the representative golf club is determined, and from these numbers, Performance Index (e.g., Bi.2) for the representative golf club is computed by using the herein mentioned polynomial formula along with representative club length, dead weight and Lpf value. The swing weight scale is based upon a 7.75 inch fulcrum and 12 inch club support. This Performance Index (e.g., Bi.2) is determined for the representative golf club to further determine alternatively the heavy versus light deviation in dead weight and balance (Lpf) for the representative golf club. Finally, the Performance Index (e.g., Bi.2) and dead weight values determined for the representative golf club are generally corresponded to at least some of the other golf clubs in a set of golf clubs, such that the system user can generally match different iron and wood golf clubs to the representative golf club, thereby creating a generally ideal matched set of golf clubs for the player.

The golf club fitting system of the present disclosure is designed to provide a relatively easy to use fitting system which is powerful in its informational and accuracy capabilities. The system/method of the present disclosure are intended to accomplish the proper fitting of clubs to player through the use of two key elements. These are as follows: a.) Club deadweight and balance are matched to each player's physical strength level, flexibility, and swing type; b.) The clubs within the player's set are weight and balance matched for more consistent on-course performance. To utilize and achieve these elements, the golf club fitting system of the present invention contemplates the following preferred step-by-step procedure for fitting, variations of which will be discussed following this description of the procedure.

Figure 1A:
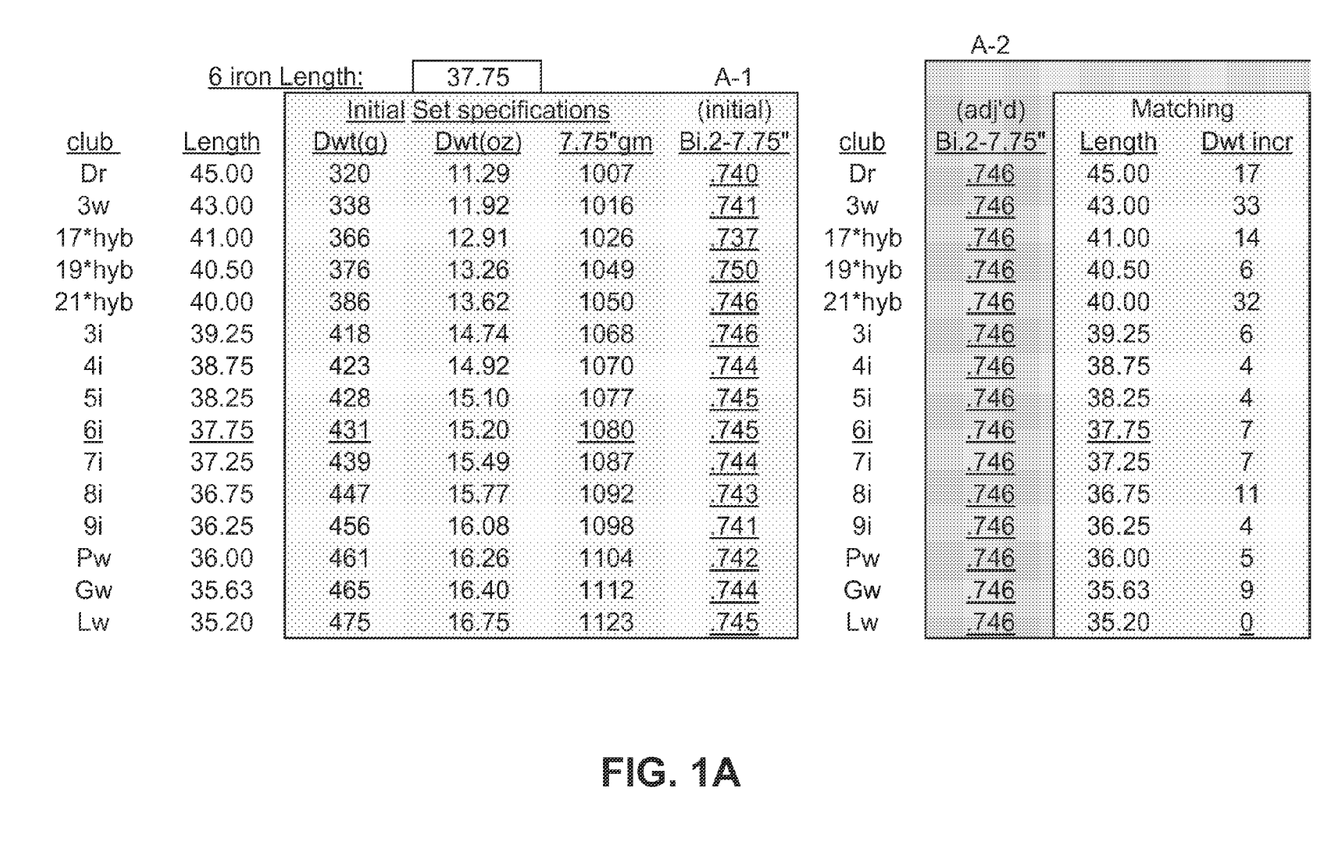
FIGS. 1A and 1B depict a spreadsheet which includes: Balance Index values for a set of golf clubs which have been leverage matched using a conventional, 14-inch fulcrum, 21-inch club support swing weight scale, and Performance Index (e.g., Bi.2) readings for the same set of golf clubs having been leverage matched using the unique 7.75-inch fulcrum, 12-inch club support swing weight scale described herein, and conventional 14-inch fulcrum Lorythmic swing weight readings for the clubs which were leverage matched using the 7.75-inch fulcrum, 12-inch club support swing weight scale.
Figure 1B:
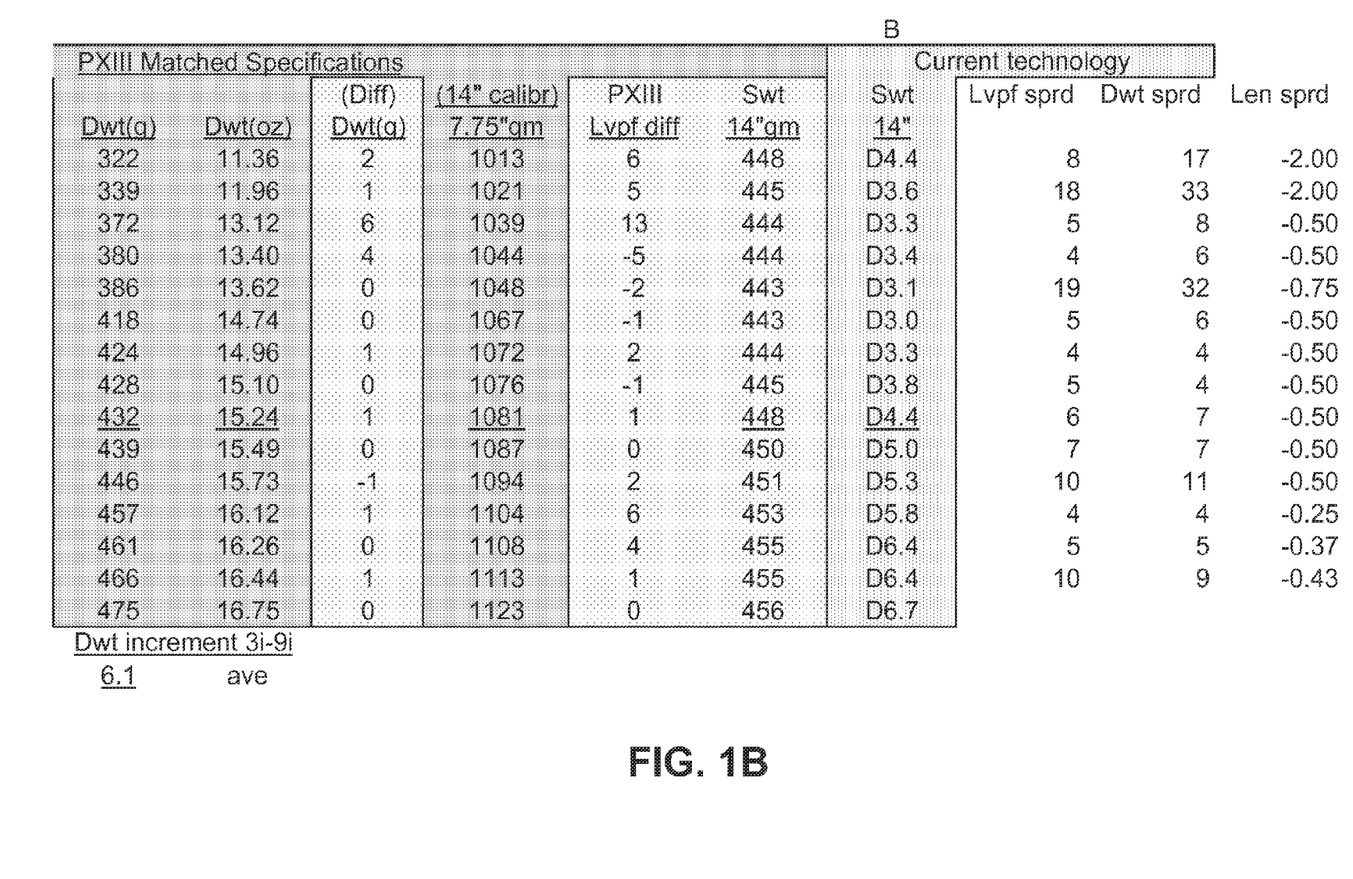

As mentioned above, the golf club fitting system of the present disclosure implements a unique swing weight scale, which is based upon a 7.75 inch fulcrum and 12 inch club support. Referring to FIGS. 1A and 1B, a spreadsheet is shown which lists in column A-1, the Performance Index values (e.g., Bi.2 readings) for a set of golf clubs which have been leverage matched using a conventional, 14-inch fulcrum, 21-inch club support swing weight scale. As can be seen, significant variations in Performance Index values (e.g., Bi.2 readings) exist between clubs when using the conventional swing weight scale. In terms of performance, these variations translate into a difference in feel and leverage against a player during the swing. Because golfers instinctively react to what they feel during the swing, these difference(s)/variation(s) in feel can and do substantially affect a player's on-course performance and consistency. In contrast, column A-2 of the spreadsheet shown in FIGS. 1A and 1B lists the Performance Index (e.g., Bi.2) readings for the same set of golf clubs having been leverage matched using the unique 7.75-inch fulcrum, 12-inch club support swing weight scale described herein. As can be seen, no variations in Performance Index (e.g., Bi.2) readings exist between clubs when using the unique swing weight described herein. The column labeled "Current Technology" shows conventional 14-inch fulcrum Lorythmic swing weight readings for the clubs which were leverage matched using the 7.75-inch fulcrum, 12-inch club support swing weight scale and also shows the comparative inaccuracy of the 14-inch fulcrum Lorythmic swing weight scale.

Figure 3:
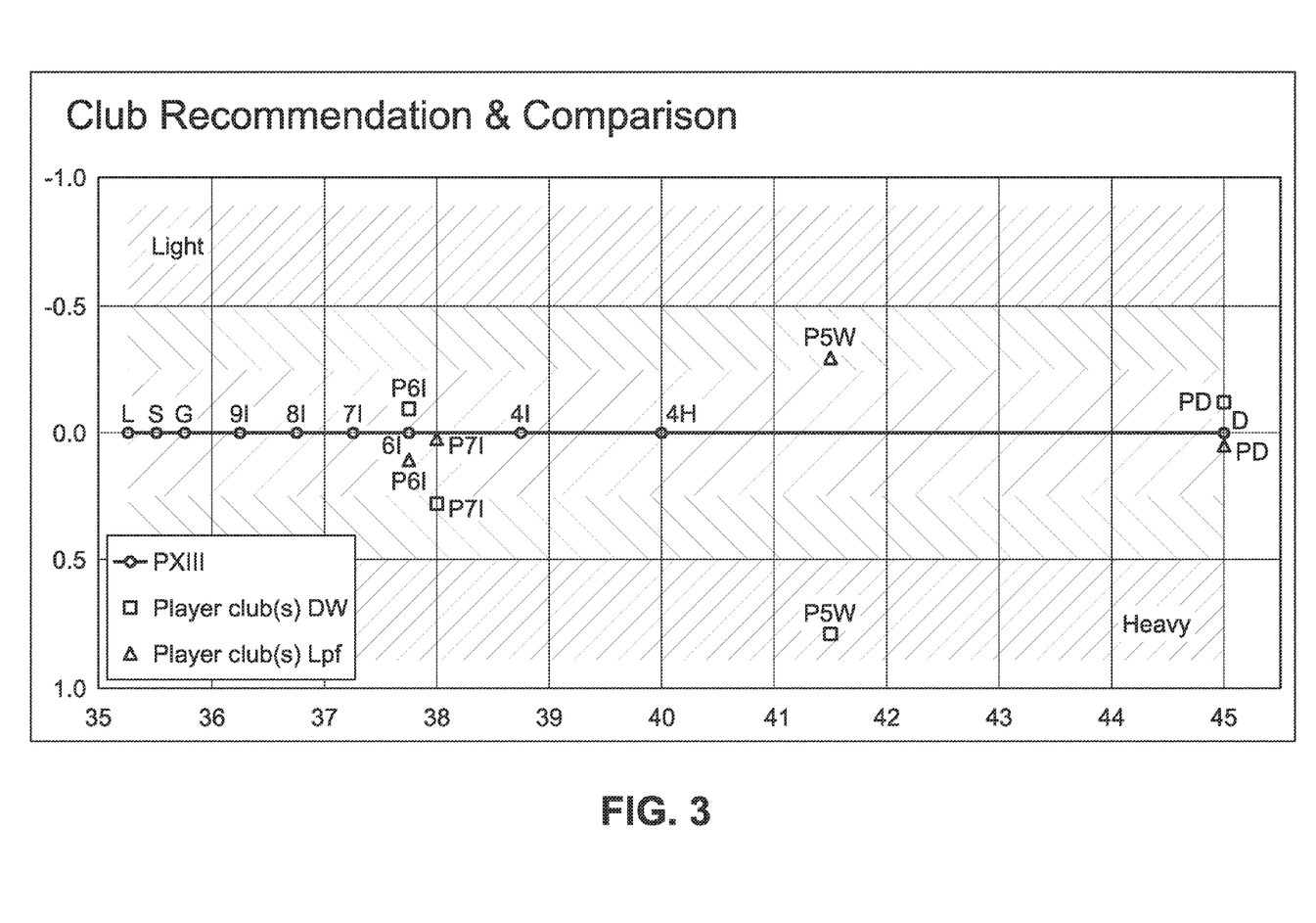
FIG. 3 depicts a fitting chart based upon the golf club fitting system/method described herein, which implements the 7.75-inch fulcrum, 12-inch club support swing scale in accordance with a further exemplary embodiment of the present disclosure.

Referring to FIG. 3, in accordance with a further embodiment of the present disclosure, a fitting chart based upon a golf club fitting system/method described herein (e.g., PXIII method/process), is shown. In embodiments, the Performance Index (e.g., Bi.2) readings are determined by a polynomial equation which utilizes all three leverage producers of a club when it is swung, the three leverage producers being: dead weight (Dwt), the Lpf reading from the 7.75-inch scale (which replaces the swing weight (Swt) value, and club length. The Performance Index (e.g., Bi.2 value(s)) is/are represented by the center horizontal line on the chart in FIG. 3. Heavy and light labels of the chart in FIG. 3 can refer to dead weight, as well as the balance of the club.

In some embodiments, the golf club fitting system and method can further include a swing analyzer. The swing analyzer comprises one or more sensors configured to detect one or more motion parameters of the club when swung (e.g., acceleration, velocity, local magnetic field, etc.). In embodiments, the swing analyzer can include an accelerometer that can measure accelerations in one or more axes. The swing analyzer can further include a gyroscope that can measure angular velocity along one or more axes. The swing analyzer can further include a magnetometer that can measure the local magnetic field along one or more axes. The information obtained from these sensors can be used to compute one or more performance indicators about the representative golf club (e.g., swing speed, club position, club orientation, etc.). For example, by compiling information obtained from the accelerometer, the gyroscope, and the magnetometer, an approximate position and orientation of the club handle and club head during the swing event can be determined.

In implementations, the swing analyzer can be removably coupled to the vent hole of the grip of a golf club. In some embodiments, the shank of the swing analyzer can comprise non-circular cross sections (e.g. ovular, square, triangular, etc.) to couple with the vent hole and prevent rotation.

In some embodiments, the swing analyzer can further include an embedded rechargeable battery to provide power to the swing analyzer. The rechargeable battery can be charged with a portable docking station. However, the use of a docking station is offered by way of example only and is not meant to be restrictive of the present disclosure. In other implementations, other charging devices can be used (e.g., USB cable, etc.).

Figure 2:
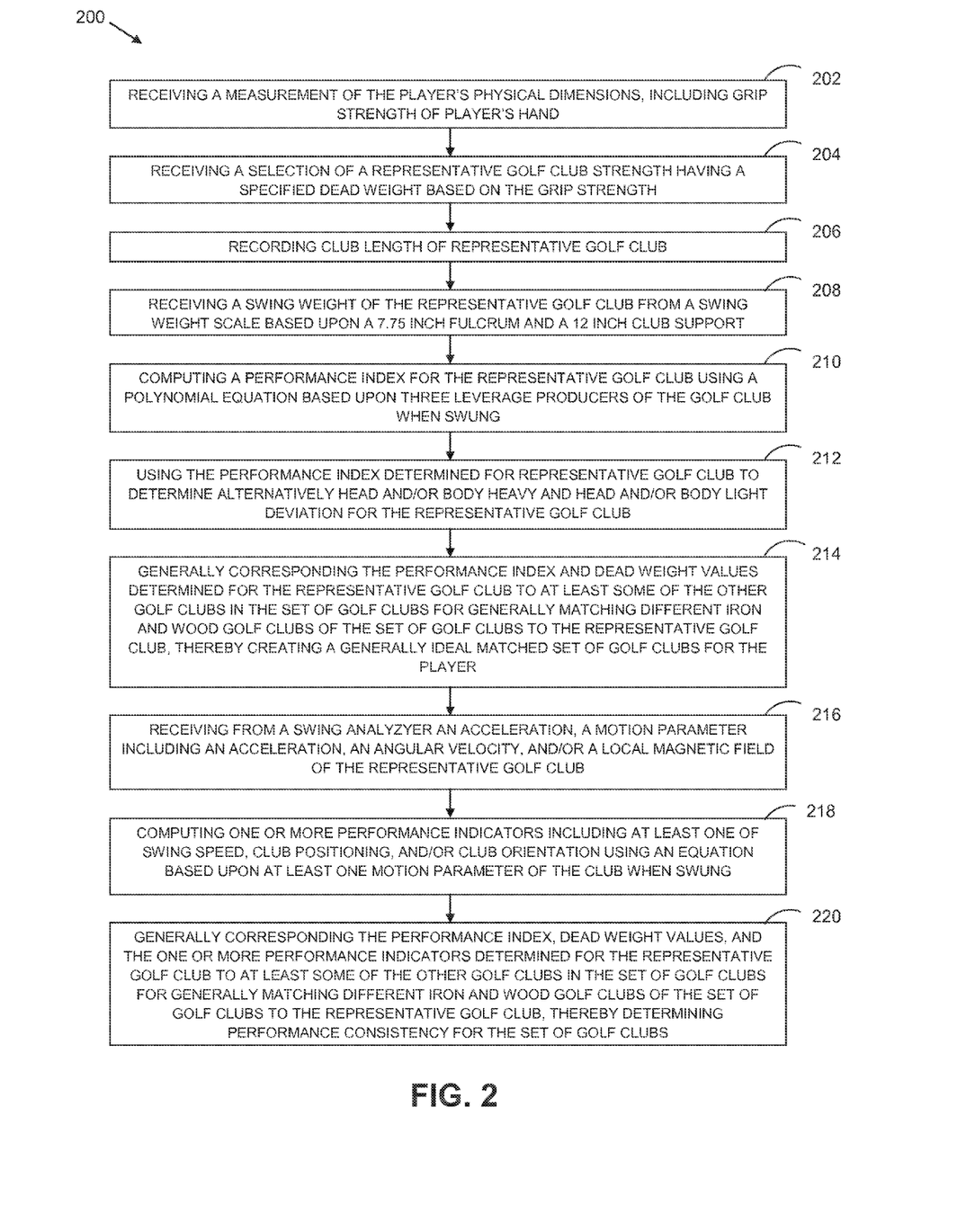
FIG. 2 is a flow chart depicting a method for fitting a set of golf clubs to a player.

Referring to FIG. 2, a flow chart depicting a method for fitting a set of golf clubs to a player, as described herein, is shown. The method 200 includes a step of receiving a measurement of the player's physical dimensions, including at least grip strength of the player's hand (Step 202). For example, measuring the player's physical dimensions can include measuring the player's middle finger length, palm-to-wrist-crease length, grip strength, player's height, ground-to-palm distance for the player's hand, and ground-to-knuckle distance of the player's longest finger. These measurements may be input into a client device (e.g., a client device 304 described below). The method 200 further includes receiving a selection of a representative golf club having a specific dead weight based in part on the measured grip strength of the player's hand, said dead weight being directly proportional to the player's grip strength. (Step 204).

The method 200 further includes the step of receiving a recordation of a club length of the representative golf club (Step 206). The method 200 further includes receiving a swing weight of the representative golf club from a swing weight scale based upon a 7.75 inch fulcrum and a 12 inch club support (Step 208). The method 200 further includes computing a Performance Index (e.g., Bi.2) for the representative golf club using a polynomial equation based upon all three leverage producers of the golf club when swung, including: dead weight, club length and a reading from the 7.75-inch fulcrum, 12-inch club support swing weight scale (e.g., Lpf reading) (Step 210). The method 200 further includes, using the Performance Index (e.g., Bi.2) determined for the representative golf club to determine alternatively head or body heavy and head or body light deviation for the representative golf club (Step 212). The method 200 further includes generally corresponding the Performance Index (e.g., Bi.2) and dead weight values determined for the representative golf club to at least some of the other golf clubs in the set of golf clubs for generally matching different iron and wood golf clubs of the set of golf clubs to the representative golf club, thereby creating a generally ideal matched set of golf clubs for the player. (Step 214).

The method further includes receiving from a swing analyzer at least one motion parameter including an acceleration, an angular velocity, and/or a local magnetic field of the representative golf club (Step 216). The method further includes computing one or more performance indicators including at least one of swing speed, club positioning, and/or club orientation using an equation based upon at least one motion parameter of the club when swung, including: acceleration, angular velocity, and/or the local magnetic field of the representative golf club (Step 218). The method further includes generally corresponding the Performance Index, dead weight values, and the one or more performance indicators determined for the representative golf club to at least some of the other golf clubs in the set of golf clubs for generally matching different iron and wood golf clubs of the set of golf clubs to the representative golf club, thereby determining performance consistency for the set of golf clubs (Step 220).

The method 200 can further include a step of conducting a player profile interview with the player to collect player information at least including: physical limitations of the player, whether the player is right or left handed, current playing ability, the player's interpretation of their game, the player's goals for their game and for fitting (Step 222).

The method 200 can further include a step of determining a preferred club head and club shaft configuration for the player at least factoring a recommended shaft length taken from an applicable fitting chart, shaft material options available, adjustments due to player, core-loading, swing tempo, shaft loading, and over-swing effects and additional grip weight due to size recommendations (Step 224). This step may be performed according to the procedures described in co-owned U.S. Pat. No. 7,195,565 entitled: "Golf Club Fitting System" which is herein incorporated by reference in its entirety.

In embodiments, the step of selecting a representative golf club includes selecting a test golf club having a determined dead weight, swing weight and balance calculated via said determining step, said test golf club having a club head including an adjustable weighting mechanism and an adjustable weight positioning mechanism, said test golf club further having a shaft length adjustment mechanism, such that the weight and balance of the club head of the test golf club and the length of the shaft of the test golf club are adjustable to fit the player's determined swing characteristics.

In embodiments, the shaft length and head weight of the test golf club is adjustable via a plurality of shaft extensions which are designed to releasably connect to the top end of the test golf club and are made in a series of progressively lengthened units, said head weights adapted to be releasably mounted into the club head of the test golf club, the head weights being in progressively heavier units, such that a precise weight and shaft length for the test golf club can be set so that the player and fitter can determine the best fitting club for the player by finding the best fit shaft length and dead weight for the best fitting club and using the resulting Performance Index (e.g., Bi.2) and dead weight figures to fit the rest of the desired set.

Figure 4:
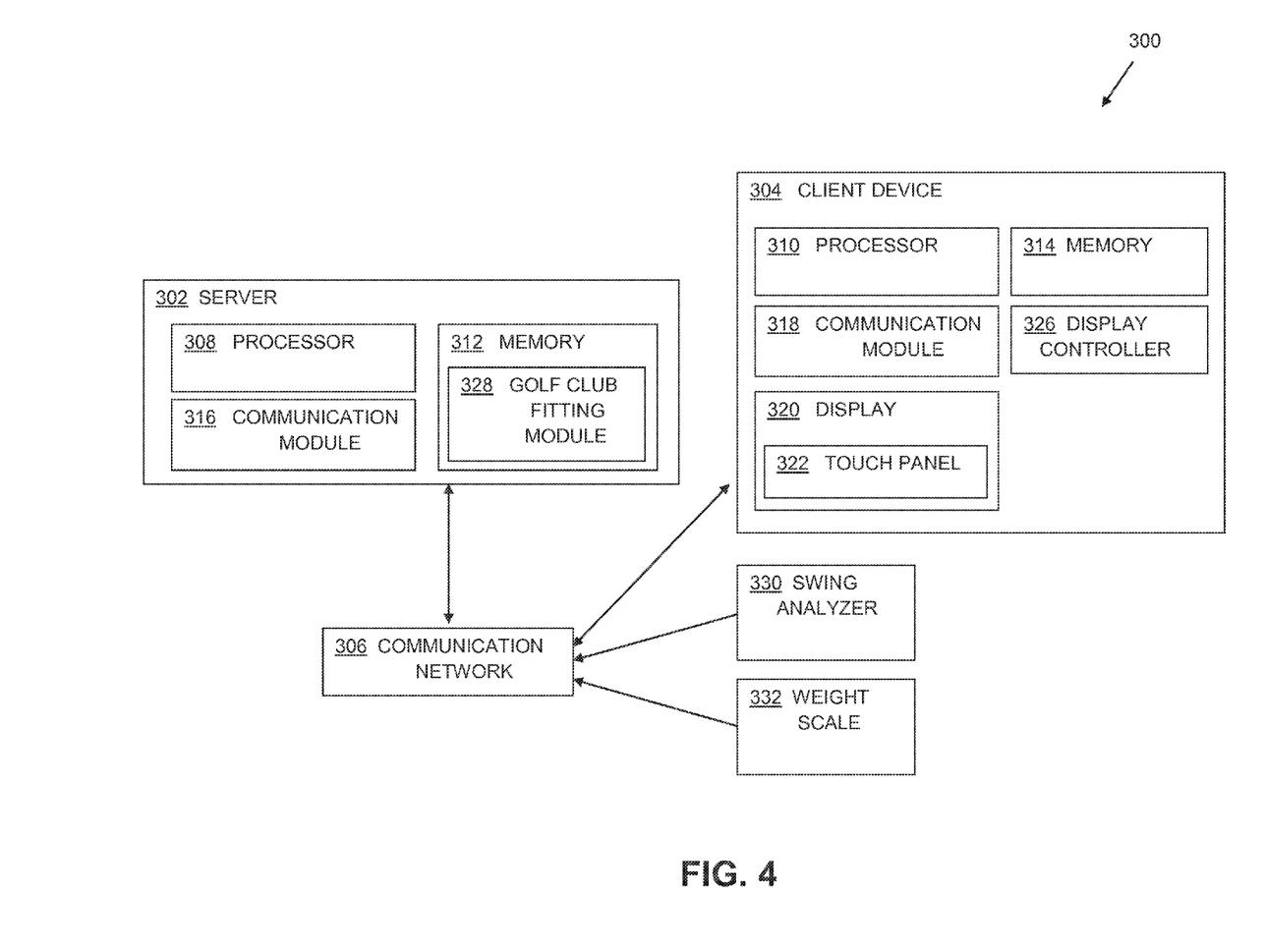
FIG. 4 is a block diagram of a golf club fitting system in accordance with an example embodiment of the present disclosure.

FIG. 4 illustrates a golf club fitting system 300 for facilitating communication between one or more client devices 304 via a communication network 306 to generate custom fitting of golf clubs in accordance with the functionality described above. In one or more implementations, the client device 304 is a mobile electronic device, such as a mobile phone (e.g., a smartphone), a tablet computer, a personal digital assistant (PDA), a desktop computer, or the like.

As shown in FIG. 4, the server 302 and the client device 304 each include a respective processor 308, 310 and a respective memory 312, 314. The processors 308, 310 provide processing functionality for the server 302 and the client device 304, respectively. The processors 308, 310 may include any number of processors, micro-controllers, or other processing systems, and resident or external memory for storing data and other information accessed or generated by the server 302 and/or the client device 304. The processors 308, 310 may execute one or more software programs (e.g., modules) that implement techniques described herein.

The memory 312, 314 is an example of tangible computer-readable media that provides storage functionality to store various data associated with the operation of the server 302 and the client device 304, software code described herein, or other data to instruct the processors 308, 310 and other elements of the server 302 or the client device 304 to perform the steps described herein. Although a single memory 312, 314 is shown within the server 302 and the client device 304, a wide variety of types and combinations of memory may be employed. The memory 312, 314 may be integral with the respective processor 308, 310, stand-alone memory, or a combination of both. The memory may include, for example, removable and non-removable memory elements such as RAM, ROM, Flash (e.g., SD Card, mini-SD card, micro-SD Card), magnetic, optical, USB memory devices, and so forth.

The server 302 is communicatively coupled to the client device 304 over a communication network 306 via communication modules 316, 318, which are included in the server 302 and the client device 304, respectively. The communication modules 316, 318 may be representative of a variety of communication components and functionality, including, but not limited to: one or more antennas; a browser; a transmitter and/or receiver (e.g., radio frequency circuitry); a wireless radio; data ports; software interfaces and drivers; networking interfaces; data processing components; and so forth.

The communication network 306 may comprise a variety of different types of networks and connections that are contemplated, including, but not limited to: the Internet; an intranet; a satellite network; a cellular network; a mobile data network; wired and/or wireless connections; and so forth.

Wireless networks may comprise any of a plurality of communications standards, protocols and technologies, including, but not limited to: Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS), and/or Short Message Service (SMS), or any other suitable communication protocol.

As shown in FIG. 4, the client device 304 may include a touch-sensitive display 320, which can be implemented using a liquid crystal display, an organic light emitting diode display, or the like. In some embodiments, the touch-sensitive display 320 may include a touch panel 322. The touch panel 322 may be, but is not limited to: a capacitive touch panel, a resistive touch panel, an infrared touch panel, combinations thereof, and the like. Thus, the display 320 may be configured to receive input from a user and display information to the user of the client device 304. For example, the display 320 displays visual output to the user. The visual output may include graphics, text, icons, video, and any combination thereof (collectively termed "graphics").

The display 320 is communicatively coupled to a display controller 324 that is configured to receive and/or transmit electrical signals to the touch-sensitive display 320. In an implementation, the touch panel 322 includes a sensor, an array of sensors, or the like, configured to accept input from a user based upon haptic and/or tactile contact. The touch panel 322, in combination with the display controller 324 (along with any associated modules and/or sets of computer-readable instructions in memory 314), detects a point of contact (or points of contact), as well as any movement or breaking of the contact, on the touch panel 322 and converts the detected contact (e.g., a finger of the user, a stylus, etc.) into electrical signals representing interactions with user-interface objects (e.g., buttons, custom views, icons, web pages, images, web page links, etc.) that are displayed via the display 320.

FIG. 4 illustrates the server 302 including a golf club fitting module 328, which is storable in memory 312 and executable by the processor 308. The golf club fitting module 328 is representative of functionality to calculating (e.g., fitting) a set of golf clubs to a player. For example, the module 328 is representative of functionality to fit a set of golf clubs to a player as discussed above with respect to FIG. 2 and the method 200 based upon input provided through a client device 304. For example, a user may input, through a client device 304, the player's physical dimensions, the representative golf club selection, and so forth. The module 328 may then instruct the processor 308 to fit a set of golf clubs utilizing the process described above with respect to FIG. 2.

The module 328 is also representative of the functionality to determine performance consistency of the set of golf clubs as discussed above with respect to FIG. 2 and the method 200. For example, the processor can receive information from a swing analyzer 330 and/or a weight scale 332. The module 328 can cause the processor 308 to determine one or more performance indicators, as described above. The module 328 may then instruct the processor 308 to determine performance consistency of the set of set of golf clubs using the process described above with respect to FIG. 2. The module 328 can also cause the communication module 316 to transmit one or more performance indicators (e.g., swing speed, club position, club orientation, etc.) to the client device 304 for display to the player.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A method for fitting a set of golf clubs to a player, the method comprising:
receiving, at a processor, a measurement of physical dimensions of the player, including at least grip strength of the player's hand;
receiving a selection comprising a representative golf club having a specific dead weight based on the measured grip strength of the player's hand, the dead weight being directly proportional to the player's grip strength;
receiving a record of a club length of the representative golf club;
receiving, from a swing weight scale, a swing weight of the representative golf club, the swing weight scale based upon a 7.75 inch fulcrum and a 12 inch club support;
computing, by way of the processor, a Performance Index for the representative golf club using a polynomial equation based upon three leverage producers of the golf club when swung, the three leverage producers comprising the dead weight, the swing weight, and the club length;
using the Performance Index determined for the representative golf club to determine alternatively head and/or body heavy and head and/or body light deviation for the representative golf club;
corresponding the Performance Index and dead weight values determined for the representative golf club to at least some of the other golf clubs in the set of golf clubs for generally matching different iron and wood golf clubs of the set of golf clubs to the representative golf club, thereby creating a generally ideal matched set of golf clubs for the player;
receiving from a swing analyzer at least one of acceleration, angular velocity, or local magnetic field of the representative golf club;
computing, by way of the processor, one or more performance indicators including at least one of swing speed, club positioning, or club orientation using an equation based upon one or more motion parameters of the club when swung, the one or more motion parameters comprising the at least one of acceleration, angular velocity, or local magnetic field of the representative golf club; and
corresponding the Performance Index, dead weight values, and the one or more performance indicators determined for the representative golf club to at least some of the other golf clubs in the set of golf clubs for generally matching different iron and wood golf clubs of the set of golf clubs to the representative golf club, thereby determining performance consistency for the set of golf clubs.

2. An apparatus comprising:
a memory operable to store one or more modules; and
a processor operable to execute the one or more modules to:
record a club length of a representative golf club;
receive, from a swing weight scale, a swing weight of the representative golf club, the swing weight scale based upon a 7.75 inch fulcrum and a 12 inch club support;
compute a Performance Index for the representative golf club using a polynomial equation based upon three leverage producers of the golf club when swung, the three leverage producers comprising a dead weight corresponding to a measured grip strength of a hand of a player, the swing weight of the representative golf club, and the club length of the representative golf club;
use the Performance Index determined for the representative golf club to determine alternatively head and/or body heavy and head and/or body light deviation for the representative golf club;
correspond the Performance Index and dead weight values determined for the representative golf club to at least some of the other golf clubs in the set of golf clubs for generally matching different iron and wood golf clubs of the set of golf clubs to the representative golf club to create a generally ideal matched set of golf clubs for the player, wherein the dead weight values correspond to a specific dead weight based on a measured grip strength of a player's hand, the specific dead weight being directly proportional to the player's grip strength;
receive from a swing analyzer at least one of acceleration, angular velocity, or local magnetic field of the representative golf club;
compute one or more performance indicators including at least one of swing speed, club positioning, or club orientation using an equation based upon one or more motion parameters of the club when swung, the one or more motion parameters comprising the at least one of acceleration, angular velocity, or local magnetic field of the representative golf club; and correspond the Performance Index, dead weight values, and the one or more performance indicators determined for the representative golf club to at least some of the other golf clubs in the set of golf clubs for generally matching different iron and wood golf clubs of the set of golf clubs to the representative golf club, thereby determining performance consistency for the set of golf clubs.

3. The apparatus as recited in claim 2, wherein the processor is operable to execute the one or more modules to receive a measurement of physical dimensions of the player, the measurement including at least grip strength of the player's hand.

4. The apparatus as recited in claim 3, wherein the processor is operable to execute the one or more modules to receive a selection of the representative golf club having a specific dead weight based on the measured grip strength of the player's hand.

5. The apparatus as recited in claim 3, wherein the processor is operable to execute the one or more modules to receive player profile characteristics.

6. The apparatus as recited in claim 2, wherein physical dimensions of the player are received from a client device communicatively coupled to the apparatus.

7. The apparatus as recited in claim 6, wherein the client device comprises at least one of a laptop computing device, a desktop computing device, or a mobile electronic computing device.

8. A system comprising:
a swing weight scale based upon a 7.75 inch fulcrum and a 12 inch club support;
a computing device communicatively coupled to the swing weight scale, the computing device comprising:
a memory operable to store one or more modules; and
a processor operable to execute the one or more modules to:
record a club length of a representative golf club;
receive, from a swing weight scale, a swing weight of the representative golf club;
compute a Performance Index for the representative golf club using a polynomial equation based upon three leverage producers of the golf club when swung, the three leverage producers comprising a dead weight corresponding to a measured grip strength of a hand of a player, the swing weight of the representative golf club, and the club length of the representative golf club;

use the Performance Index determined for the representative golf club to determine alternatively head and/or body heavy and head and/or body light deviation for the representative golf club;
correspond the Performance Index and dead weight values determined for the representative golf club to at least some of the other golf clubs in the set of golf clubs for generally matching different iron and wood golf clubs of the set of golf clubs to the representative golf club to create a generally ideal matched set of golf clubs for the player, wherein the dead weight values correspond to a specific dead weight based on a measured grip strength of a player's hand, the specific dead weight being directly proportional to the player's grip strength;
receive from a swing analyzer at least one of acceleration, angular velocity, or local magnetic field of the representative golf club;
compute one or more performance indicators including at least one of swing speed, club positioning, or club orientation using an equation based upon one or more motion parameters of the club when swung, the one or more motion parameters comprising the at least one of acceleration, angular velocity, or local magnetic field of the representative golf club; and
correspond the Performance Index, dead weight values, and the one or more performance indicators determined for the representative golf club to at least some of the other golf clubs in the set of golf clubs for generally matching different iron and wood golf clubs of the set of golf clubs to the representative golf club, thereby determining performance consistency for the set of golf clubs.

9. The system as recited in claim 8, wherein the processor is operable to execute the one or more modules to receive a measurement of physical dimensions of the player, the measurement including at least grip strength of the player's hand.

10. The system as recited in claim 9, wherein the processor is operable to execute the one or more modules to receive a selection of the representative golf club having a specific dead weight based on the measured grip strength of the player's hand.

11. The system as recited in claim 9, wherein the processor is operable to execute the one or more modules to receive player profile characteristics.

12. The system as recited in claim 8, wherein physical dimensions of the player are received from a client device communicatively coupled to the apparatus.

* * * * *